United States Patent
Park et al.

(10) Patent No.: US 11,382,519 B2
(45) Date of Patent: Jul. 12, 2022

(54) BLOOD PRESSURE MEASURING APPARATUS AND BLOOD PRESSURE MEASURING METHOD

(71) Applicant: SAMSUNG ELECTRONICS CO., LTD., Suwon-si (KR)

(72) Inventors: Sang Yun Park, Hwaseong-si (KR); Jae Min Kang, Seoul (KR); Yong Joo Kwon, Yongin-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 630 days.

(21) Appl. No.: 16/266,672

(22) Filed: Feb. 4, 2019

(65) Prior Publication Data
US 2019/0239758 A1 Aug. 8, 2019

(30) Foreign Application Priority Data

Feb. 5, 2018 (KR) .................. 10-2018-0014218

(51) Int. Cl.
*A61B 5/021* (2006.01)
*A61B 5/00* (2006.01)
(Continued)

(52) U.S. Cl.
CPC ...... *A61B 5/02116* (2013.01); *A61B 5/02108* (2013.01); *A61B 5/02416* (2013.01);
(Continued)

(58) Field of Classification Search
CPC .. A61B 5/02108–02116; A61B 5/6826; A61B 5/1172; A61B 5/6831; A61B 5/681;
(Continued)

(56) References Cited

U.S. PATENT DOCUMENTS 4,394,773 A * 7/1983 Ruell .................. A61B 5/1172
310/318
9,028,418 B2 5/2015 Parzy et al.
(Continued)

FOREIGN PATENT DOCUMENTS

GB 2551201 A * 12/2017 ........... A61B 5/0261
JP 61292786 A * 12/1986
(Continued)

OTHER PUBLICATIONS

Translation of Item N (JP-61292786-A) from EPO Patent Translate (Year: 2021).*

*Primary Examiner* — Eric F Winakur
*Assistant Examiner* — Alice Ling Zou
(74) *Attorney, Agent, or Firm* — Sughrue Mion, PLLC

(57) ABSTRACT

A blood pressure measuring apparatus may include: a touch sensor; a pulse wave measurer configured to measure pulse waves from a user's finger when the user's finger is in contact with the touch sensor; a contact pressure measurer configured to measure a contact pressure between the user's finger and the touch sensor; a fingerprint recognizer configured to recognize a fingerprint of the user's finger; and a processor configured to determine a degree of position coincidence between the user's finger and the pulse wave measurer based on the recognized fingerprint, and to estimate a blood pressure of the user based on the pulse waves and the contact pressure according to the determined degree of position coincidence.

15 Claims, 15 Drawing Sheets

(51) Int. Cl.
*A61B 5/024* (2006.01)
*A61B 5/1172* (2016.01)
*G06V 40/12* (2022.01)

(52) U.S. Cl.
CPC .......... *A61B 5/6826* (2013.01); *A61B 5/6843* (2013.01); *A61B 5/1172* (2013.01); *A61B 5/681* (2013.01); *A61B 5/6831* (2013.01); *G06V 40/12* (2022.01)

(58) Field of Classification Search
CPC . A61B 5/022; A61B 5/02225; A61B 5/02255; A61B 2562/0247; A61B 2562/0252; A61B 2562/0261; A61B 5/7221; A61B 5/021–02125; A61B 5/024; A61B 5/02416–2444; A61B 5/0255; A61B 5/70; A61B 5/6843–6844; A61B 5/02; G06K 9/00006; G06K 9/0002; G06K 9/00087; G06K 9/00093; G06K 9/001; G06K 9/00013; G06F 2203/04105; G06F 3/0445–0446; G06F 3/0414–04146
See application file for complete search history.

(56) References Cited

U.S. PATENT DOCUMENTS

| | | |
|---|---|---|
| 2002/0026121 A1 | 2/2002 | Kan |
| 2006/0079791 A1 | 4/2006 | Letremy et al. |
| 2008/0095412 A1* | 4/2008 | Fujieda ................ A61B 5/1172 382/124 |
| 2009/0174671 A1* | 7/2009 | Tachi ..................... G06F 3/016 345/173 |
| 2010/0324388 A1 | 12/2010 | Moon et al. |
| 2011/0282219 A1 | 11/2011 | Parzy et al. |
| 2012/0190944 A1 | 7/2012 | Thaveeprungsriporn et al. |
| 2012/0283583 A1 | 11/2012 | Batkin et al. |
| 2014/0198071 A1* | 7/2014 | Algreatly ............ G06F 3/04815 345/173 |
| 2015/0374249 A1 | 12/2015 | Elliot et al. |
| 2016/0051193 A1* | 2/2016 | Park ....................... A61B 5/681 600/300 |
| 2017/0095168 A1* | 4/2017 | Kwon .................. A61B 5/0261 |
| 2017/0119262 A1 | 5/2017 | Shim et al. |
| 2018/0177413 A1 | 6/2018 | Kwon et al. |

FOREIGN PATENT DOCUMENTS

| | | |
|---|---|---|
| JP | 2006-239114 A | 9/2006 |
| JP | 2012-510840 A | 5/2012 |
| KR | 10-2006-0081178 A | 7/2006 |
| KR | 10-2015-0057185 A | 5/2015 |
| KR | 10-2017-0049279 A | 5/2017 |
| WO | 2015151132 A1 | 10/2015 |
| WO | WO-2017152098 A1 * | 9/2017 ............. A61B 5/022 |

* cited by examiner

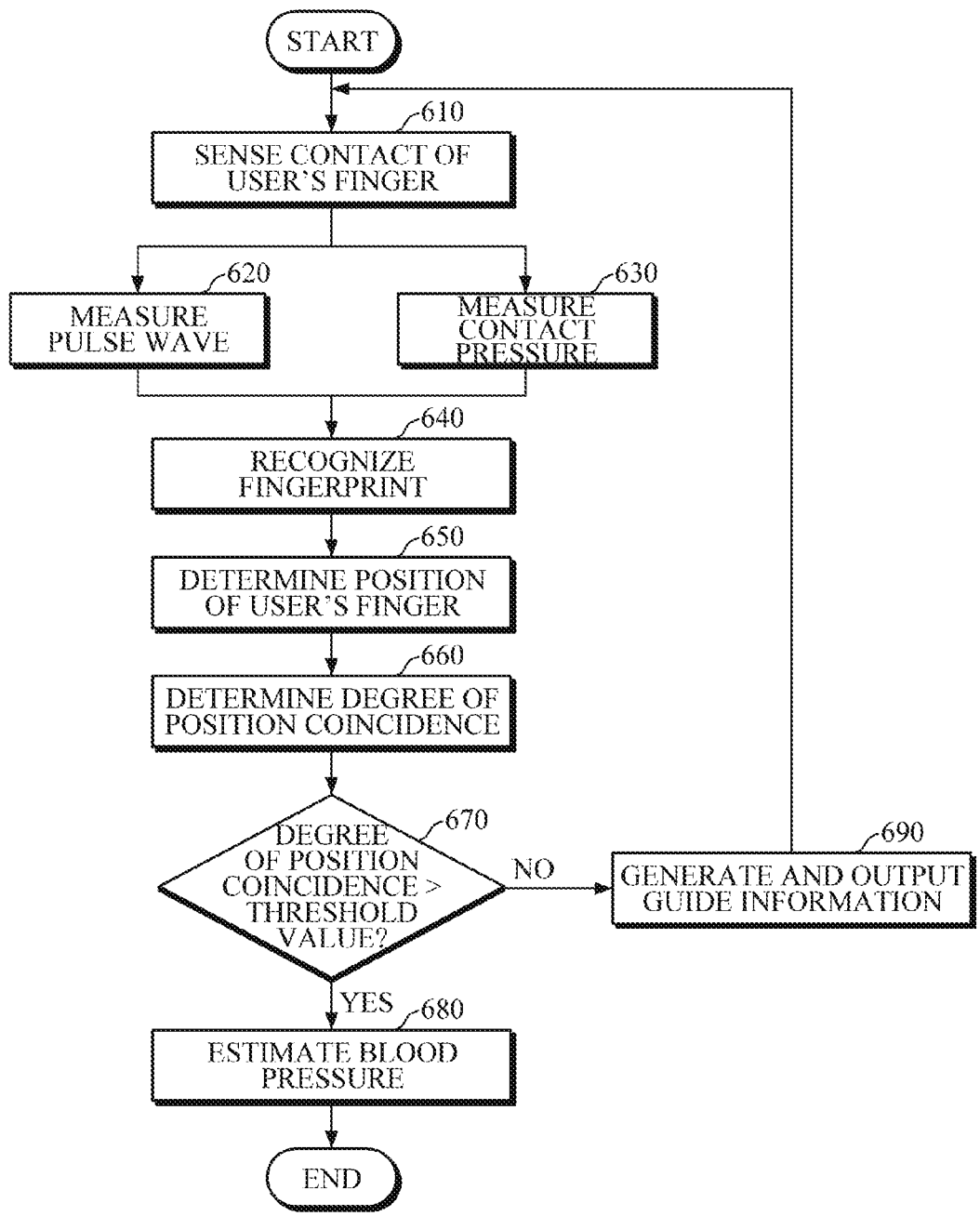

BLOOD PRESSURE MEASURING APPARATUS AND BLOOD PRESSURE MEASURING METHOD

CROSS-REFERENCE TO RELATED APPLICATION(S)

This application claims priority from Korean Patent Application No. 10-2018-0014218, filed on Feb. 5, 2018, in the Korean Intellectual Property Office, the disclosure of which is incorporated herein by reference in its entirety.

BACKGROUND

1. Field

Apparatuses and methods consistent with exemplary embodiments relate to cuffless blood pressure measurement.

2. Description of the Related Art

A pressurized cuff is generally used for measuring blood pressure. A blood pressure measuring method utilizing the pressurized cuff is a non-continuous measuring method, in which the cuff is inflated so that an artery is constricted up to around systolic blood pressure, and then the pressure in the cuff is slowly released. However, the pressurized cuff includes a booster pump and the like, such that the cuff is unsuitable for use in a mobile device.

Recently, research has been conducted on blood pressure measuring apparatuses for cufflessly measuring blood pressure in a non-pressure manner without using a cuff, and examples thereof include a blood pressure measuring apparatus using Pulse Transit Time (PTT) and a blood pressure measuring apparatus using Pulse Wave Analysis (PWA). However, the blood pressure measuring apparatus using PTT is inconvenient in that correction is required for each user to ensure accuracy of measurement; and since bio-signals should be measured at two or more locations to measure the pulse wave velocity, the apparatus cannot be manufactured in a compact size. Further, the blood pressure measuring apparatus using PWA estimates blood pressure by analyzing only a pulse wave form, such that the PWA is vulnerable to noise, and blood pressure may not be measured with improved accuracy.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an apparatus and method for cufflessly measuring blood pressure with improved accuracy.

According to an aspect of an exemplary embodiment, there is provided a blood pressure measuring apparatus including: a touch sensor; a pulse wave measurer configured to measure pulse waves from a user's finger when the user's finger is in contact with the touch sensor; a contact pressure measurer configured to measure a contact pressure between the user's finger and the touch sensor; a fingerprint recognizer configured to recognize a fingerprint of the user's finger; and a processor configured to determine a degree of position coincidence between the user's finger and the pulse wave measurer based on the recognized fingerprint, and to estimate a blood pressure of the user based on the pulse waves and the contact pressure according to the determined degree of position coincidence.

The touch sensor may include a first area for recognizing the fingerprint and a second area that surrounds the first area.

The first area may have a higher resolution than a resolution of the second area.

The fingerprint recognizer may recognize the fingerprint by using a sensor value of the first area.

The contact pressure measurer may include: a contact force measurer configured to measure a contact force between the user and the touch sensor; a contact area measurer configured to measure a contact area between the user's finger and the touch sensor; and a contact pressure calculator configured to calculate the contact pressure based on the contact force and the contact area.

The pulse waves may include photoplethysmogram.

The processor may determine a position of the user's finger based on the recognized fingerprint, and may determine the degree of position coincidence between the user's finger and the pulse wave measurer based on the determined position of the user's finger.

The processor may determine the position of the user's finger by comparing the recognized fingerprint with pre-stored reference fingerprint information.

The processor may determine the degree of position coincidence between the user's finger and the pulse wave measurer by determining whether a central portion of the user's finger is positioned on the pulse wave measurer based on the determined position of the user's finger.

In response to the determined degree of position coincidence exceeding a predetermined threshold value, the processor may estimate blood pressure of the user. In response to the determined degree of position coincidence not exceeding the predetermined threshold value, the processor may discard the measured pulse waves In response to the determined degree of position coincidence being less than or equal to a predetermined threshold value, the processor may generate guide information for changing a position of the user's finger, may adjust reliability of a pre-estimated blood pressure estimation value, or may discard the pre-estimated blood pressure estimation value.

The processor may obtain additional information on a contact state between the user's finger and the touch sensor by using the touch sensor, and upon a determination of whether the obtained additional information satisfies a predetermined criterion, the processor may estimate the blood pressure of the user based on the pulse waves and the contact pressure.

The additional information may include at least one of a contact area between the user's finger and the touch sensor, a shape of a contact surface, and a center of gravity of the contact surface.

In response to the obtained additional information satisfying the predetermined criterion, the processor may estimate the blood pressure of the user.

In response to the obtained additional information not satisfying the predetermined criterion, the processor may generate guide information for changing a position of the user's finger, may adjust reliability of the pre-estimated blood pressure estimation value, or may discard the pre-estimated blood pressure estimation value.

According to an aspect of another exemplary embodiment, there is provided a blood pressure measuring method including: sensing contact between a user's finger and a touch sensor; measuring, using a pulse wave measurer, pulse waves from the user's finger when the user's finger is in contact with the touch sensor; measuring contact pressure between the user's finger and the touch sensor; recognizing a fingerprint of the user's finger; determining a degree of position coincidence between the user's finger and the pulse wave measurer based on the recognized fingerprint; and estimating a blood pressure of the user based on the pulse waves and the contact pressure according to the determined degree of position coincidence.

The touch sensor may include a first area for recognizing the fingerprint and a second area that surrounds the first area; and the first area may have a higher resolution than a resolution of the second area.

The recognizing the fingerprint may include recognizing the fingerprint by using a sensor value of the first area.

The determining of the degree of position coincidence may include: determining a position of the user's finger by comparing the recognized fingerprint with pre-stored reference fingerprint information; and determining the degree of position coincidence between the user's finger and the pulse wave measurer by determining whether a central portion of the user's finger is positioned on the pulse wave measurer based on the determined position of the user's finger.

The estimating the blood pressure of the user may include: in response to the determined degree of position coincidence exceeding a predetermined threshold value, estimating blood pressure of the user; and in response to the determined degree of position coincidence being less than or equal to the predetermined threshold value, generating guide information for changing a position of the user's finger, adjusting reliability of a pre-estimated blood pressure estimation value, or discarding the pre-estimated blood pressure estimation value.

BRIEF DESCRIPTION OF THE DRAWINGS

The above and/or other aspects will be more apparent by describing certain exemplary embodiments, with reference to the accompanying drawings, in which:

FIG. 6 is a flowchart illustrating a blood pressure estimating method according to an exemplary embodiment;

DETAILED DESCRIPTION

Figure 1:
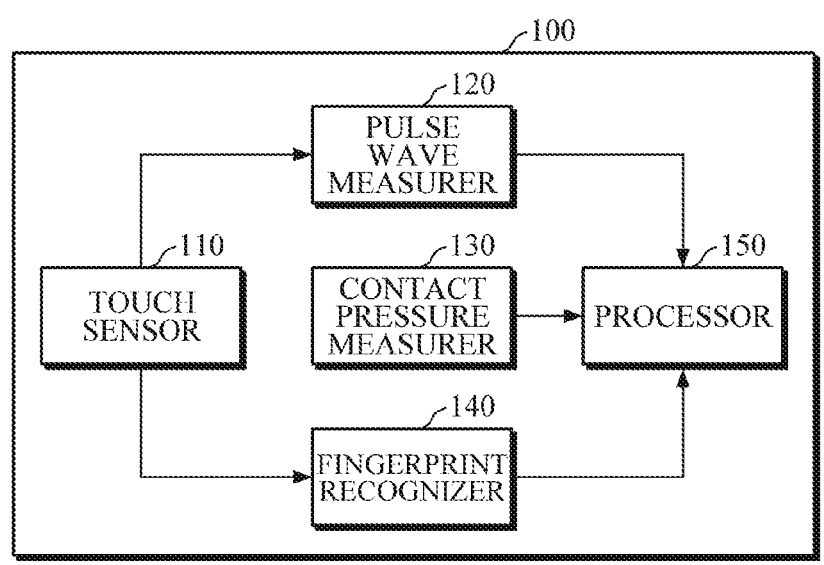
FIG. 1 is a block diagram illustrating a blood pressure measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Throughout the drawings and the detailed description, unless otherwise described, the same drawing reference numerals will be understood to refer to the same elements, features, and structures. The relative size and depiction of these elements may be exaggerated for clarity, illustration, and convenience.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, bh, and c.

Figure 2:
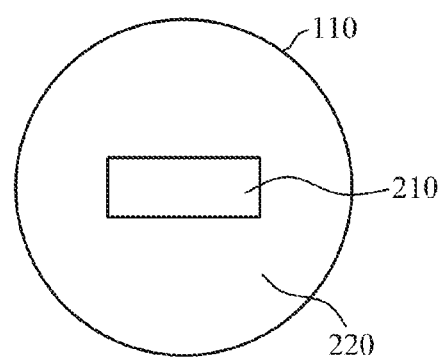
FIG. 2 is a diagram explaining a touch area of a touch sensor 110 of FIG. 1 according to an exemplary embodiment.
Figure 3:
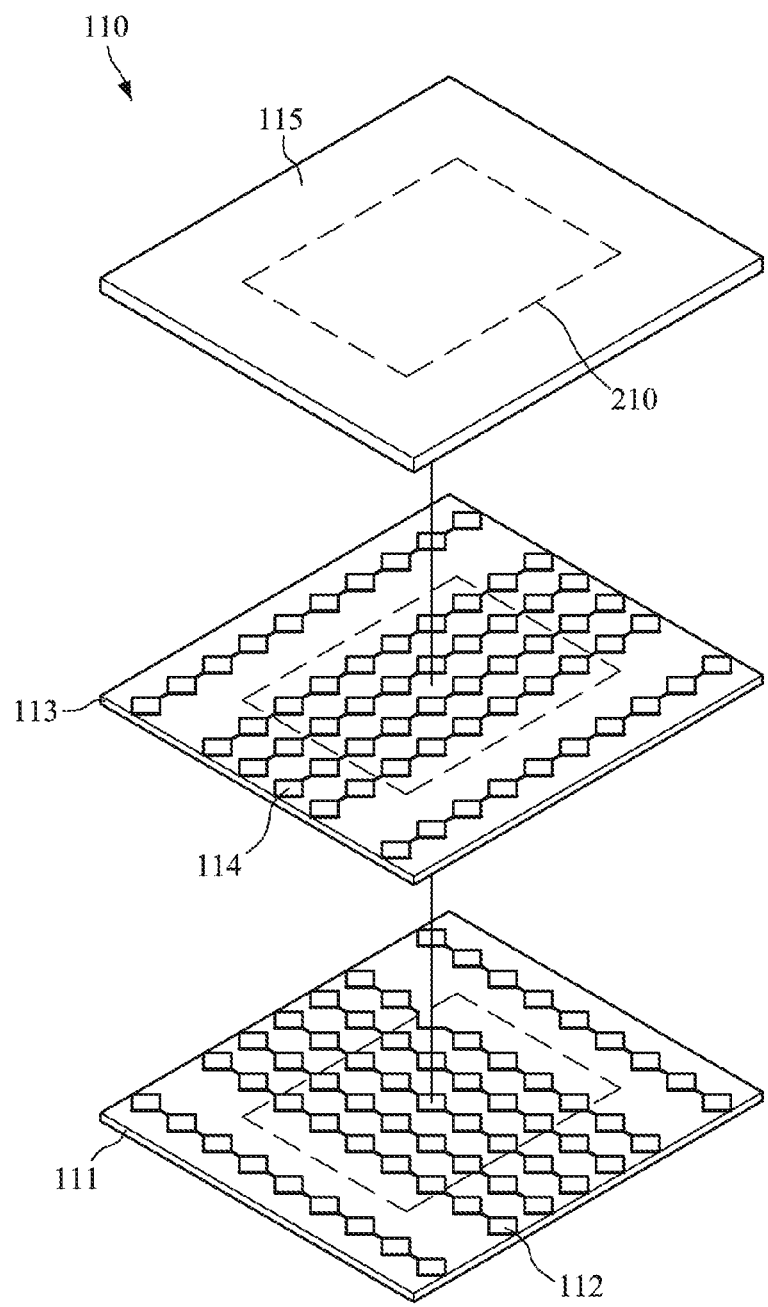
FIG. 3 is an exploded perspective diagram of the touch sensor 110 of FIG. 1 according to an exemplary embodiment.
Figure 4:
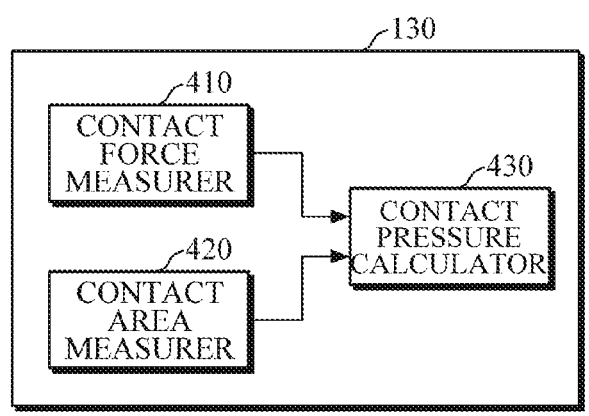
FIG. 4 is a block diagram illustrating a contact pressure measurer 130 of FIG. 1 according to an exemplary embodiment.

FIG. 1 is a block diagram illustrating a blood pressure measuring apparatus according to an exemplary embodiment; FIG. 2 is a diagram explaining a touch area of a touch sensor 110 of FIG. 1 according to an exemplary embodiment; FIG. 3 is an exploded perspective diagram of the touch sensor 110 of FIG. 1 according to an exemplary embodiment; and FIG. 4 is a block diagram illustrating a contact pressure measurer 130 of FIG. 1 according to an exemplary embodiment. The blood pressure measuring apparatus 100 of FIG. 1 may be implemented as a software module or manufactured in the form of a hardware chip to be embedded in various types of electronic devices. In this case, examples of the electronic devices may include a cellular phone, a smartphone, a tablet personal computer (PC), a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 1, the blood pressure measuring apparatus 100 includes a touch sensor 110, a pulse wave measurer 120, a contact pressure measurer 130, a fingerprint recognizer 140, and a processor 150.

The touch sensor 110 is disposed at an outermost portion of the blood pressure measuring apparatus 100 to sense contact of a user's finger. In one exemplary embodiment, the touch sensor 110 may include a capacitance-type touch sensor.

Sensor values of the touch sensor 110 may be used to recognize a user's fingerprint, a contact area between a user's finger and the touch sensor 110, a shape of a contact surface, a center of gravity of the contact surface, and the like. In order to increase accuracy of fingerprint recognition, a touch sensor having a high resolution may be used. However, a touch sensor having a relatively low resolution may be used as long as the relatively low resolution is sufficient to recognize a contact area between a user's finger and the touch sensor, a shape of a contact surface, a center of gravity of the contact surface, and the like. Therefore, the touch sensor 110 may be able to provide a high accuracy fingerprint recognition even when the resolution of the entire touch area of the touch sensor 110 is low.

In an exemplary embodiment, the touch area of the touch sensor 110 may be divided into at least two areas according to resolution. For example, as illustrated in FIG. 2, the touch area of the touch sensor 110 may be divided into a first area 210, having a relatively high resolution, and a second area 220 having a relatively low resolution. In particular, sensor values sensed in the first area 210 may be used to recognize a user's fingerprint; and sensor values sensed in the second area 220 may be used to recognize a contact area of a user, a shape of a contact surface, a center of gravity of the contact surface, and the like. The second area 220 may be located to surround the first area 210.

Referring to FIG. 3, the touch sensor 110 includes a transparent substrate 111, sensing lines 112 arranged in a plurality of rows on the transparent substrate 111, a transparent insulating layer 113 covering the sensing lines 112, driving lines 114 arranged in a plurality of columns on the transparent insulating layer 113, and a transparent cover 115 covering the driving lines 114.

The transparent substrate 111 may be made of transparent plastic, transparent glass, or the like, to have light transmission and insulation properties. The transparent substrate 111 may support the sensing lines 112.

The sensing lines 112 and the driving lines 114 may be made of a transparent conductive material such as Indium Tin Oxide (ITO), carbon nanotube, and the like. The sensing lines 112 and the driving lines 114 may intersect with each other to form a grid. An intersecting point of the sensing lines 112 and the driving lines 114 may be a pair of coordinates.

The sensing lines 112 may have electrode pads which are connected by a bridge. Here, each of the electrode pads may be formed in a diamond shape. The bridge may have a much narrower width than the electrode pads. In the same manner as the sensing lines 112, the driving lines 114 may have electrode pads which are connected by a bridge. The sensing lines 112 and the driving lines 114 may be arranged so that the bridges thereof may intersect with each other. Accordingly, two electrode pads of the sensing lines 112 and two electrode pads of the driving lines 114 may be arranged based on intersecting points of the bridges.

The transparent insulating layer 113 may insulate between the sensing lines 112 and the driving lines 114. The transparent insulating layer 113 may be made of a material having light transmission and insulation properties.

The transparent cover 115 may be made of transparent plastic, transparent glass, or the like, to have light transmission and insulation properties. The transparent cover 115 may protect the driving lines 114. The transparent cover 115 may be adhered to the transparent insulating layer 113 while covering the driving lines 114.

A space interval between the sensing lines 112 and a space interval between the driving lines 114 may be formed to be narrower than the second area 220 so that the first area 210 may have a higher resolution than the second area 220.

Although FIGS. 2 and 3 illustrate an example where the touch area of the touch sensor 110 is divided into two areas 210 and 220, and the first area 210 is positioned at the center of the touch area of the touch sensor 110, the touch area of the touch sensor 110 is not limited thereto. That is, the touch area of the touch sensor 110 may be divided into three or more areas according to performance and purpose of use of a system. Further, according to performance and purpose of use of a system, the first area 210 having the highest resolution may be positioned on a top portion, a bottom portion, a left portion, a right portion, and the like, of the touch area of the touch sensor 110.

The pulse wave measurer 120 may be disposed below the touch sensor 110, and may measure pulse waves of a user by transmitting and receiving light to and from a user's finger touching the touch sensor 110. In this case, the pulse waves may include photoplethysmogram and the like. To this end, the pulse wave measurer 120 may include a light emitter and a light receiver.

The light emitter may emit light onto the user's finger touching the touch sensor 110. The light emitter may include one or more light sources including a light emitting diode (LED), a laser diode, a fluorescent body, or the like.

In an exemplary embodiment, each of the light sources may emit a visible ray, a Near Infrared Ray (NIR), or a Mid Infrared Ray (MIR). However, wavelengths of light emitted from the light sources may vary depending on the purpose of measurement or the types of target components to be analyzed. Each of the light sources is not limited to a single light-emitting body, and may include an array of a plurality of light-emitting bodies. Each of the light sources may emit light of the same wavelength, or light of different wavelengths.

The light receiver may receive light reflected or scattered from a user's finger. The light receiver may include one or more photodetectors including a photo diode, a photo transistor (PTr), a charge-coupled device (CCD), or the like. The photodetector is not limited to a single device, but may include an array of a plurality of devices.

Various numbers and arrangements of light sources and photodetectors may be provided, and the number and arrangement thereof may vary depending on the purpose of use of the pulse wave measurer 120, the size and shape of the electronic device including the blood pressure measuring apparatus 100, and the like.

The contact pressure measurer 130 may be disposed below the pulse wave measurer 120, and may measure contact pressure between a user's finger and the touch sensor 110. The contact pressure measurer 130 may transmit the measured contact pressure between the user's finger and the touch sensor 110 to the processor 150, so that the measured contact pressure between the user's finger and the touch sensor 110 may be used to estimate blood pressure as external pressure acting on blood vessels. To this end, the contact pressure measurer 130 may include a contact force measurer 410, a contact area measurer 420, and a contact pressure calculator 430, as illustrated in FIG. 3.

The contact force measurer 410 may measure a contact force between a user's finger and the touch sensor 110. The contact force may be exerted to the touch sensor 110 by the user's finger. To this end, the contact force measurer 410 may include a force sensor and the like. In an exemplary embodiment, the contact force measurer 410 may be disposed below the pulse wave measurer 120.

The contact area measurer 420 may measure a contact area between a user's finger and the touch sensor 110. In an exemplary embodiment, the contact area measurer 420 may measure a contact area between the user's finger and the touch sensor 110 by using sensor values sensed by the touch sensor 110.

While a sensing current is sequentially supplied to the driving lines 114 of the touch sensor 110, when a user touches with a finger a top portion of the transparent cover 115, capacitance may be changed at intersecting points touched by the finger, among intersecting points of the sensing lines 112 and the driving lines 114. In this case, the contact area measurer 420 may obtain coordinates of each of the intersecting points, located at an outermost position, among the intersecting points where capacitance is changed, and may calculate a contact area of the finger based on the obtained coordinate information.

The contact pressure calculator 430 may calculate contact pressure (contact pressure=contact force/contact area) between a user's finger and the touch sensor 110 based on the contact force measured by the contact force measurer 410 and the contact area measured by the contact area measurer 420. Specifically, the contact pressure calculator 430 may calculate the contact pressure based on the following equation:

$$P=F/A,$$

wherein P denotes the contact pressure, F denotes the contact force, and A denotes the contact area.

The fingerprint recognizer 140 may recognize a fingerprint of a contact portion of a user's finger touching the touch sensor 110. In an exemplary embodiment, the fingerprint recognizer 140 may recognize a ridge and a valley of the contacting portion of the finger by using sensor values sensed in the first area 210 of the touch sensor 110, and may recognize a fingerprint of the contact portion of the user's finger based on the recognized ridge and valley.

The processor 150 may control the overall operations of the blood pressure measuring apparatus 100.

When a user's finger touches the touch sensor 110, the processor 150 may generate guide information for guiding contact pressure between the finger and the touch sensor 110 to be increased or decreased for measuring blood pressure, and may provide the generated guide information to the user through an output device. In this case, the output device may include at least one of a visual output device, an acoustic output device, a tactile output device, and the like.

When the user's finger touches the touch sensor 110, the processor 150 may control the pulse wave measurer 120 to measure pulse waves of the user, and may control the contact pressure measurer 130 to measure contact pressure between the user's finger and the touch sensor 110. Further, the processor 150 may estimate blood pressure of the user by analyzing a change in the pulse waves according to the measured contact pressure.

Blood pressure may include diastolic blood pressure (DBP), systolic blood pressure (SBP), and mean arterial pressure (MAP); and the contact pressure applied to the finger may act as external pressure on blood vessels. In the case where the contact pressure is lower than the MAP, an elastic restoring force of tissues act to constrict blood vessels, such that the amplitude of a pulse wave signal is reduced; and in the case where the contact pressure is equal to the MAP, the elastic restoring force of tissues becomes zero, having no effect on blood vessels, such that the amplitude of a pulse wave signal reaches its peak value. Further, in the case where the contact pressure is greater than the MAP, the elastic restoring force of tissues act to dilate blood vessels, such that the amplitude of a pulse wave signal is reduced. Accordingly, by analyzing a change in pulse wave signals according to the contact pressure, the processor 150 may estimate that contact pressure at a peak amplitude of the pulse wave signal is the MAP. Further, the processor 150 may estimate that contact pressure, at which an amplitude has a value equal to a first percentage (e.g., 0.6) of the peak amplitude, is the systolic blood pressure (SBP); and may estimate that contact pressure, at which an amplitude has a value equal to a second percentage (e.g., 0.7) of the peak amplitude, is the diastolic blood pressure (DBP).

When a user's finger touches the touch sensor 110, the processor 150 may control the fingerprint recognizer 140 to recognize a fingerprint of a contact portion of the user's finger. Further, the processor 150 may determine a position of the user's finger with respect to the pulse wave measurer 120 based on the recognized fingerprint, and may determine a degree of position coincidence between the user's finger and the pulse wave measurer 120. In this case, the processor 150 may use pre-stored user fingerprint information (hereinafter referred to as reference fingerprint information). For example, the processor 150 may determine a position of the finger by comparing pattern information of the recognized fingerprint of the contact portion of the finger with the reference fingerprint information, and may determine a degree of position coincidence between the user's finger and the pulse wave measurer 120 based on a relative position between the finger and the pulse wave measurer 120. For example, the processor 150 may determine the degree of position coincidence by determining a distance between a central portion of the finger and a center portion of the pulse wave measurer 120. Here, the term "a degree of position coincident" may be also referred to as a degree of position overlap. The processor 150 may use various similarity calculation algorithms such as Euclidean distance, Manhattan Distance, Cosine Distance, Mahalanobis Distance, Jaccard Coefficient, Extended Jaccard Coefficient, Pearson's Correlation Coefficient, Spearman's Correlation Coefficient, and the like.

The reference fingerprint information may be pre-registered by a user and may be stored in an internal or external database of the processor 150.

The processor 150 may perform predetermined functions according to the determined degree of position coincidence. In this case, the predetermined functions may include estimating blood pressure, generating and outputting guide information, adjusting reliability of a blood pressure estimation value, discarding the blood pressure estimation value and performing re-measurement, or the like.

In an exemplary embodiment, in response to the degree of position agreement between the user's finger and the pulse wave measurer 120 exceeding a predetermined threshold value, the processor 150 may estimate blood pressure of the user by analyzing a change in pulse waves according to the measured contact pressure.

In another exemplary embodiment, in response to the degree of position coincidence between the user's finger and the pulse wave measurer 120 being less than or equal to the predetermined threshold value, the processor 150 may generate guide information for changing the position of the user's finger based on the determined position of the user's finger, and may provide the generated guide information to the user through an output device. In this case, the output device may include all of a visual output device, an acoustic output device, a tactile output device, and the like.

In yet another example, in response to the degree of position coincidence between the user's finger and the pulse wave measurer 120 being less than or equal to the predetermined threshold value, the processor 150 may lower reliability of the pre-estimated blood pressure estimation value, may discard the blood pressure estimation value, and may repeat the processes of measuring pulse waves and contact pressure and estimating blood pressure. The processor 150 may adjust the reliability of the pre-estimated blood pressure value by using a model which defines a relationship between a degree of position coincidence and reliability of blood pressure estimation values.

The processor 150 may obtain additional information on contact between a user's finger and the touch sensor 110 by using sensor values of the touch sensor 110. In this case, the additional information may include a contact area between the user's finger and the touch sensor 110, a shape of a contact surface, a center of gravity of the contact surface, and the like. Further, the processor 150 may determine whether the obtained additional information satisfies a predetermined criterion; and based on determination whether the predetermined criterion is satisfied, the processor 150 may perform functions, such as estimating blood pressure, generating and outputting guide information, adjusting reliability of a blood pressure estimation value, or discarding the blood pressure estimation value and performing re-measurement. For example, in response to a contact area between the user's finger and the touch sensor 110 exceeding the predetermined threshold value, the processor 150 may estimate blood pressure by using a measured value; and in response to the contact area between the user's finger and the touch sensor 110 being less than or equal to the predetermined threshold value, the processor 150 may generate guide information thereon and may provide the generated guide information to the user through an output device, may adjust reliability of a pre-estimated blood pressure estimation value, or may discard the pre-estimated blood pressure estimation value and may perform re-measurement. In another example, in response to a shape of a contact surface between the user's finger and the touch sensor 110 being a predetermined shape, the processor 150 may estimate blood pressure by using a measured value; and in response to the shape of the contact surface between a user's finger and the touch sensor 110 not being the predetermined shape, the processor 150 may generate guide information thereon and may provide the generated guide information to a user through an output device, may lower reliability of a pre-estimated blood pressure estimation value, or may discard the pre-estimated blood pressure estimation value and may perform re-measurement. In yet another example, in response to a center of gravity of a contact surface between a user's finger and the touch sensor 110 being located at a predetermined position, the processor 150 may estimate blood pressure by using a measured value; and in response to the center of gravity of the contact surface between the user's finger and the touch sensor 110 not being located at the predetermined position, the processor 150 may generate guide information thereon and may provide the generated guide information to a user through an output device, may lower reliability of a pre-estimated blood pressure estimation value, or may discard the pre-estimated blood pressure estimation value and may perform re-measurement.

Figure 5A:
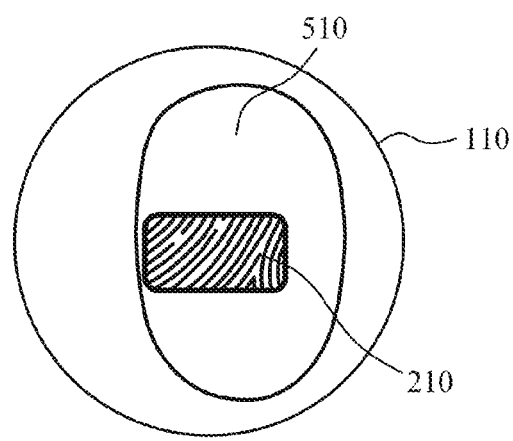
FIGS. 5A, 5B, and 5C are diagrams explaining a method of determining a position of a finger according to an exemplary embodiment.
Figure 5B:
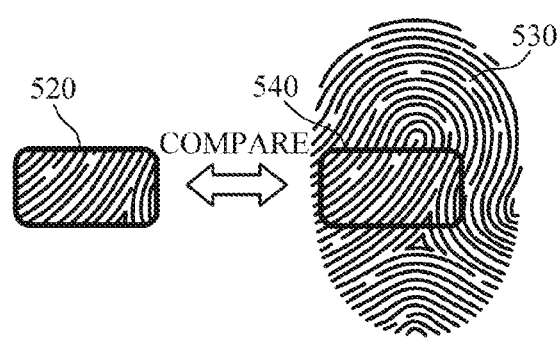
Figure 5C:
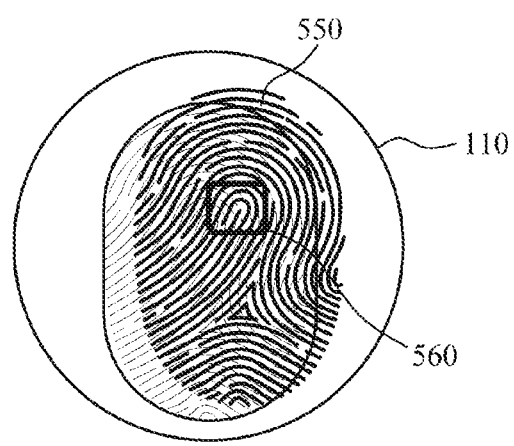

FIGS. 5A to 5C are diagrams explaining a method of determining a position of a finger according to an exemplary embodiment. In FIGS. 5A to 5C, reference numeral 510 denotes a contact area between a user's finger and the touch sensor 110.

Referring to FIGS. 1 and 5A to 5C, when a user touches with a finger the touch sensor 110, the fingerprint recognizer 140 may recognize a contact portion of a user's fingerprint 520 by using a sensor value of the first area 210 of the touch sensor 110. The processor 150 may determine a position 540 of the recognized fingerprint 520 by comparing a pattern of the user's fingerprint 520 with pre-stored reference fingerprint information 530; and based on the position 540 of the recognized fingerprint 520, the processor 150 may determine a position 550 of the user's finger.

The processor 150 may determine a degree of position coincidence between a user's finger and the pulse wave measurer 120. In response to the determined degree of position coincidence not exceeding a predetermined threshold value, the processor 150 may generate and output guide information for adjusting a position of the finger. In the illustrated example, assuming that the pulse wave measurer 120 is located at the center of the touch sensor 110, a position of a central portion 560 of the finger, which is determined based on the position 550 of the finger, is not located at the center of the touch sensor 110. Accordingly, the processor 150 may generate and output guide information for guiding the central portion 560 of the finger to be located at the center of the touch sensor 110. In this case, the guide information may be presented in the form of a graphic including an anticipated contact position and a current contact position.

FIG. 6 is a flowchart illustrating a blood pressure estimating method according to an exemplary embodiment. The blood pressure estimating method of FIG. 6 may be performed by the blood pressure measuring apparatus 100 of FIG. 1.

Referring to FIGS. 1 and 6, the blood pressure measuring apparatus 100 may sense contact of a user's finger with the touch sensor 110 in operation 610. A touch area of the touch sensor 110 may include at least two areas having different resolutions. For example, the touch area of the touch sensor 110 may include a first area 210 having a relatively high resolution, and a second area 220 having a relatively low resolution.

The blood pressure measuring apparatus 100 may measure pulse waves of a user by transmitting and receiving light to and from the user's finger touching the touch sensor 110 in operation 620. In this case, the pulse waves may include photoplethysmogram and the like.

While measuring the pulse waves, the blood pressure measuring apparatus 100 may measure contact pressure between the user's finger and the touch sensor 110 in operation 630. For example, the blood pressure measuring apparatus 100 may measure a contact force between the user's finger and the touch sensor 110, may measure a contact area between the user's finger and the touch sensor 110 by using sensor values sensed by the touch sensor 110, and may calculate a contact pressure (e.g., contact pressure=contact force/contact area) between the user's finger and the touch sensor 110 based on the measured contact force and the measured contact area.

The blood pressure measuring apparatus 100 may recognize a fingerprint of a contact portion of the user's finger touching the touch sensor 110 in operation 640. For example, the blood pressure measuring apparatus 100 may recognize a ridge and a valley of a contacting portion of a finger by using sensor values sensed in the first area 210 of the touch sensor 110, and may recognize a fingerprint of the contact portion of the finger based on the recognized ridge and valley.

The blood pressure measuring apparatus 100 may determine a position of the user's finger with respect to the pulse wave measurer 120 based on the recognized fingerprint in operation 650. In this case, the blood pressure measuring apparatus 100 may use pre-stored reference fingerprint information. For example, the blood pressure measuring apparatus 100 may determine a position of the user's finger by comparing pattern information of the recognized fingerprint of the contact portion of the finger with the reference fingerprint information.

The blood pressure measuring apparatus 100 may determine a degree of position coincidence between the user's finger and the pulse wave measurer 120 in operation 660. For example, the blood pressure measuring apparatus 100 may determine a degree of position coincidence between the user's finger and the pulse wave measurer 120 by determining whether a central portion of the finger is positioned on the pulse wave measurer 120 based on the determined position of the finger.

The blood pressure measuring apparatus 100 may compare a degree of position coincidence between the finger and the pulse wave measurer 120 with a predetermined threshold value. In response to the determined degree of position coincidence exceeding a predetermined threshold value in operation 670, the blood pressure measuring apparatus 100 may estimate blood pressure of the user by analyzing a change in pulse waves according to the measured contact pressure in operation 680.

In response to the degree of position coincidence being less than or equal to the predetermined threshold value in operation 670, the blood pressure measuring apparatus 100 may generate guide information for changing a position of the user's finger based on the determined position of the user's finger and may provide the generated guide information to the user in operation 690; and may return to operation 610 to re-sense the contact of the user's finger.

Upon sensing the contact of the user's finger, the blood pressure measuring apparatus 100 may generate guide information for guiding contact pressure between the finger and the touch sensor 110 to be increased or decreased for measuring blood pressure, and may provide the generated guide information to the user through an output device.

Figure 7:
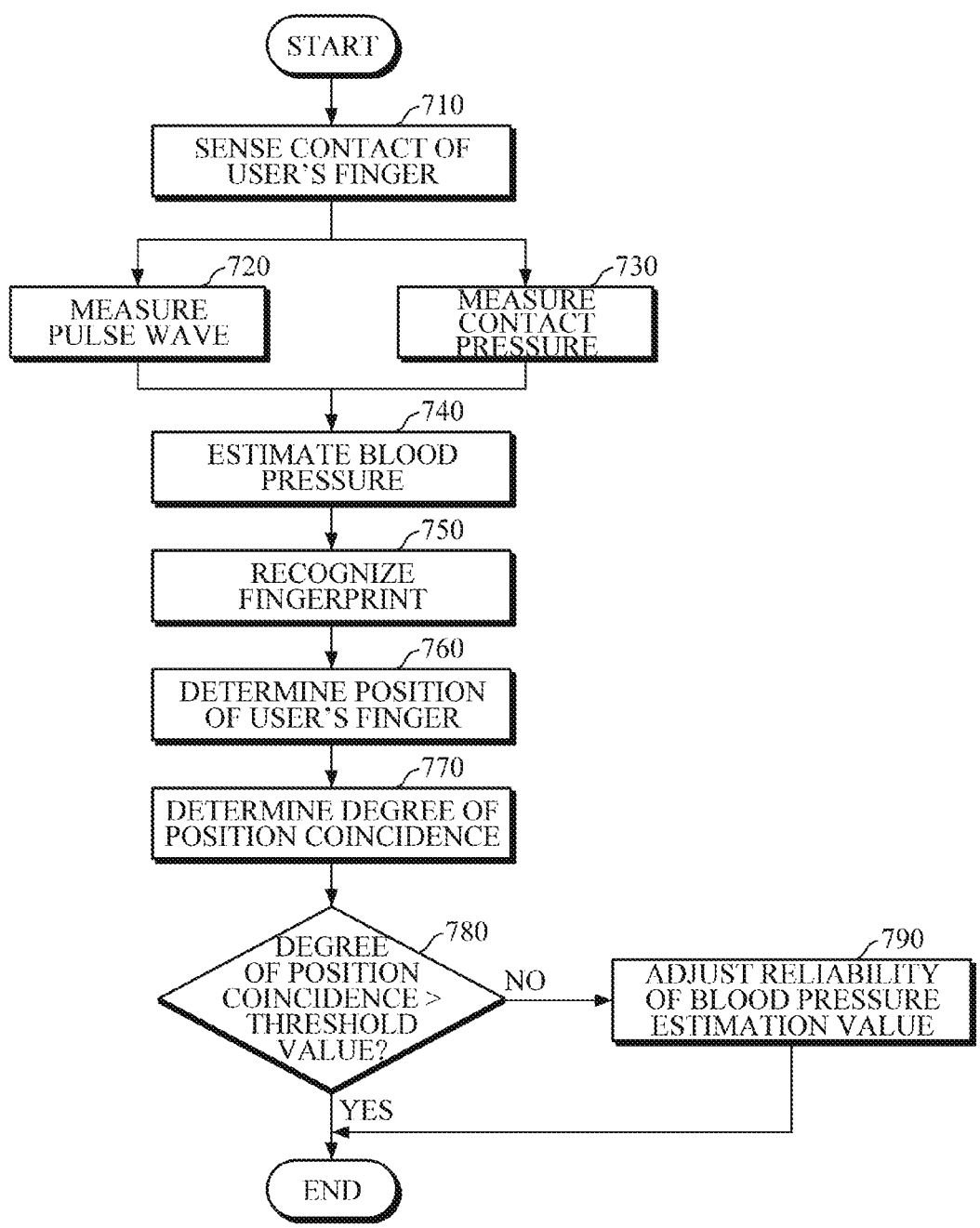
FIG. 7 is a flowchart illustrating a blood pressure estimating method according to another exemplary embodiment.

FIG. 7 is a flowchart illustrating a blood pressure estimating method according to another exemplary embodiment. The blood pressure estimating method of FIG. 7 may be performed by the blood pressure measuring apparatus 100 of FIG. 1.

Referring to FIGS. 1 and 7, the blood pressure measuring apparatus 100 may sense contact of a user's finger with the touch sensor 110 in operation 710.

The blood pressure measuring apparatus 100 may measure pulse waves of the user by transmitting and receiving light to and from the user's finger touching the touch sensor 110 in operation 720.

The blood pressure measuring apparatus 100 may measure contact pressure between the user's finger and the touch sensor 110 in operation 730.

The blood pressure measuring apparatus 100 may estimate blood pressure of the user by analyzing a change in pulse waves according to the measured contact pressure in operation 740.

The blood pressure measuring apparatus 100 may recognize a fingerprint of a contact portion of the user's finger touching the touch sensor 110 in operation 750.

The blood pressure measuring apparatus 100 may determine a position of the user's finger with respect to the pulse wave measurer 120 based on the recognized fingerprint in operation 760.

The blood pressure measuring apparatus 100 may determine a degree of position coincidence between the user's finger and the pulse wave measurer 120 in operation 770.

The blood pressure measuring apparatus 100 may compare a degree of position coincidence between the finger and the pulse wave measurer 120 with a predetermined threshold value. In response to the determined degree of position coincidence exceeding a predetermined threshold value in operation 780, the blood pressure measuring apparatus 100 may determine a blood pressure estimation value, which is estimated in operation 740, to be a final blood pressure estimation value, and may terminate a blood pressure estimating process.

In response to the degree of position coincidence between the user's finger and the pulse wave measurer 120 being less than or equal to the predetermined threshold value in operation 780, the blood pressure measuring apparatus 100 may adjust, in operation 790, reliability of the blood pressure estimation value which is estimated in 740, and may terminate a blood pressure estimating process. Also, the blood pressure measuring apparatus 100 may discard the measured pulse waves when the degree of position coincidence does not exceed the predetermined threshold value.

Figure 8:
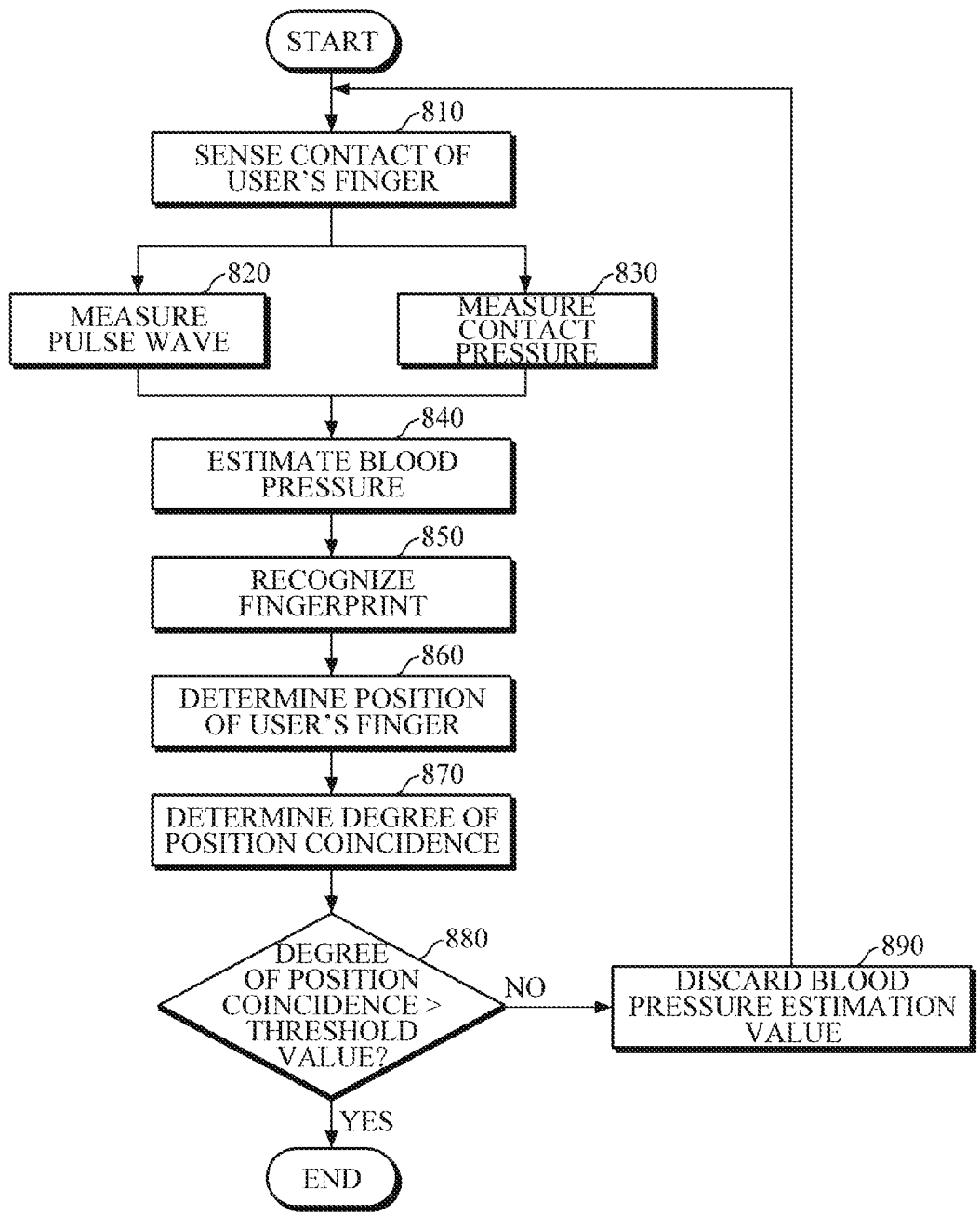
FIG. 8 is a flowchart illustrating a blood pressure estimating method according to another exemplary embodiment.

FIG. 8 is a flowchart illustrating yet another example of a blood pressure estimating method. The blood pressure estimating method of FIG. 8 may be performed by the blood pressure measuring apparatus 100 of FIG. 1.

Referring to FIGS. 1 and 8, the blood pressure measuring apparatus 100 may sense contact of a user's finger with the touch sensor 110 in operation 810.

The blood pressure measuring apparatus 100 may measure pulse waves of the user by transmitting and receiving light to and from the user touching the touch sensor 110 in operation 820.

The blood pressure measuring apparatus 100 may measure contact pressure between the user's finger and the touch sensor 110 in operation 830.

The blood pressure measuring apparatus 100 may estimate blood pressure of the user by analyzing a change in pulse waves according to the measured contact pressure in operation 840.

The blood pressure measuring apparatus 100 may recognize a fingerprint of a contact portion of the user's finger touching the touch sensor 110 in operation 850.

The blood pressure measuring apparatus 100 may determine a position of the user's finger with respect to the pulse wave measurer 120 based on the recognized fingerprint in operation 860.

The blood pressure measuring apparatus 100 may determine a degree of position coincidence between the user's finger and the pulse wave measurer 120 in operation 870.

The blood pressure measuring apparatus 100 may compare a degree of position coincidence between the finger and the pulse wave measurer 120 with a predetermined threshold value. In response to the determined degree of position coincidence exceeding a predetermined threshold value in operation 880, the blood pressure measuring apparatus 100 may determine a blood pressure estimation value, which is estimated in operation 840, to be a final blood pressure estimation value, and may terminate a blood pressure estimating process.

By contrast, in response to the degree of position coincidence between the user's finger and the pulse wave measurer 120 being less than or equal to the predetermined threshold value in operation 880, the blood pressure measuring apparatus 100 may discard, in operation 890, the blood pressure estimation value which is estimated in operation 840, and may return to operation 810 to sense contact of the user's finger.

Figure 9:
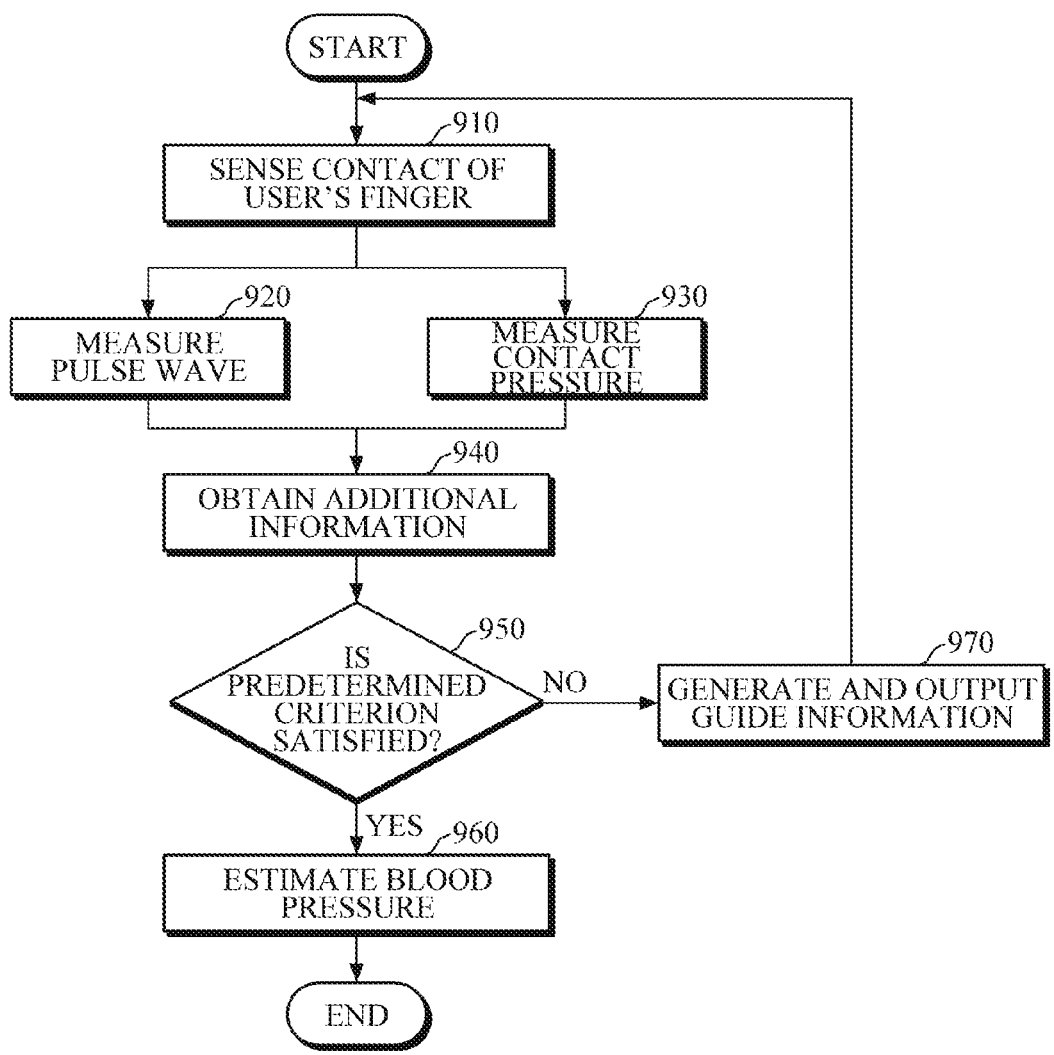
FIG. 9 is a flowchart illustrating a blood pressure estimating method according to another exemplary embodiment.

FIG. 9 is a flowchart illustrating still another example of a blood pressure estimating method. The blood pressure estimating method of FIG. 9 may be performed by the blood pressure measuring apparatus 100 of FIG. 1.

Referring to FIGS. 1 and 9, the blood pressure measuring apparatus 100 may sense contact of a user's finger with the touch sensor 110 in operation 910.

The blood pressure measuring apparatus 100 may measure pulse waves of the user by transmitting and receiving light to and from the user's finger touching the touch sensor 110 in operation 920.

The blood pressure measuring apparatus 100 may measure contact pressure between the user's finger and the touch sensor 110 in operation 930.

The blood pressure measuring apparatus 100 may obtain additional information on contact between the user's finger and the touch sensor 110 by using a sensor value of the touch sensor 110 in operation 940. In this case, the additional information may include a contact area between the user's finger and the touch sensor 110, a shape of a contact surface, a center of gravity of the contact surface, and the like.

The blood pressure measuring apparatus 100 may determine whether the obtained additional information satisfies a predetermined criterion; and upon determination, in response to the additional information satisfying the predetermined criterion in operation 950, the blood pressure measuring apparatus 100 may estimate blood pressure of the user by analyzing a change in pulse waves according to the measured contact pressure in operation 960.

By contrast, in response to the additional information not satisfying the predetermined criterion in operation 950, the blood pressure measuring apparatus 100 may generate and output guide information for changing a contact position or a contact area of the finger in operation 970, and may return to operation 910 to re-sense contact of the user's finger.

Figure 10:
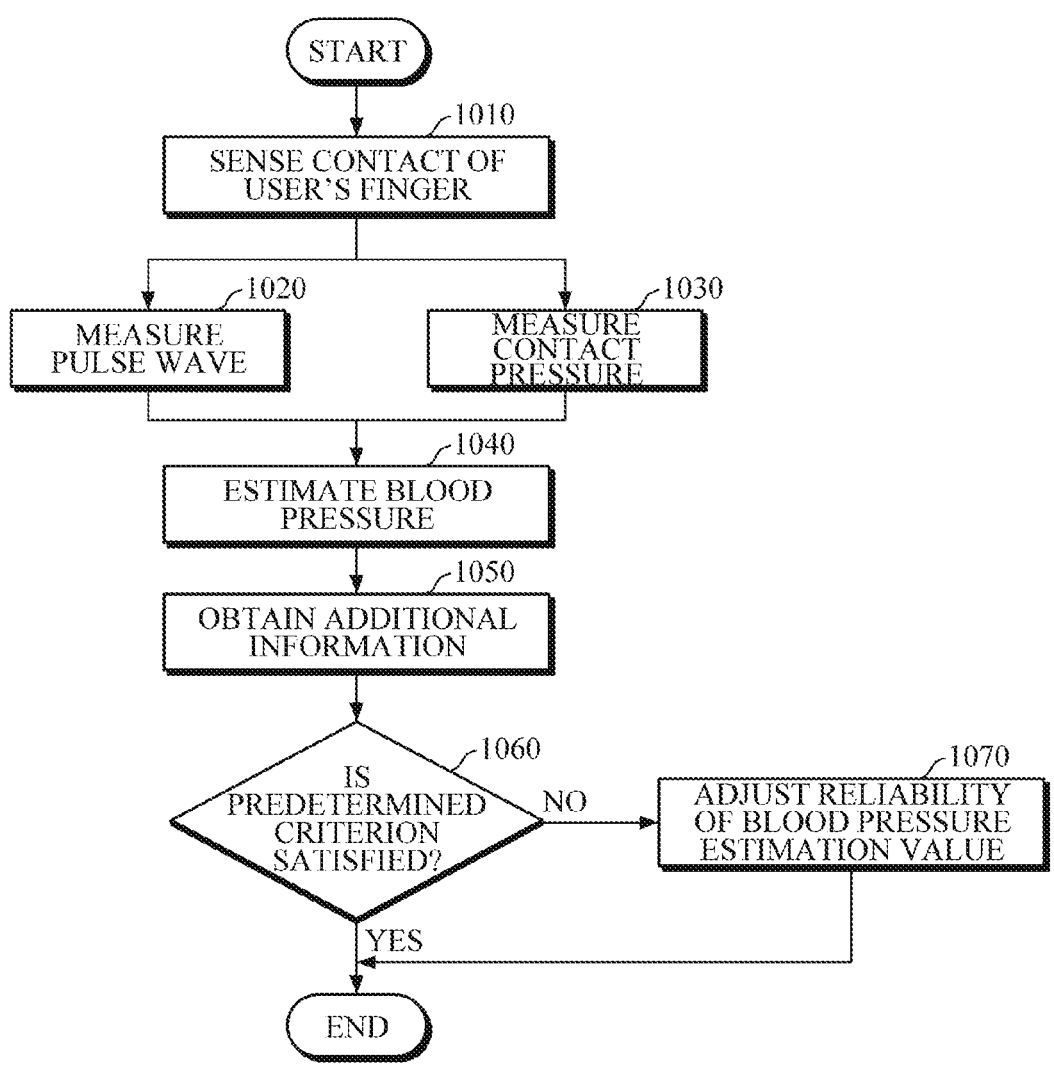
FIG. 10 is a flowchart illustrating a blood pressure estimating method according to another exemplary embodiment.

FIG. 10 is a flowchart illustrating yet another example of a blood pressure estimating method. The blood pressure estimating method of FIG. 10 may be performed by the blood pressure measuring apparatus 100 of FIG. 1.

Referring to FIGS. 1 and 10, the blood pressure measuring apparatus 100 may sense contact of a user's finger with the touch sensor 110 in operation 1010.

The blood pressure measuring apparatus 100 may measure pulse waves of the user by transmitting and receiving light to and from the user's finger touching the touch sensor 110 in operation 1020.

The blood pressure measuring apparatus 100 may measure contact pressure between the user's finger and the touch sensor 110 in operation 1030.

The blood pressure measuring apparatus 100 may estimate blood pressure of the user by analyzing a change in pulse waves according to the measured contact pressure in operation 1040.

The blood pressure measuring apparatus 100 may obtain additional information on contact between the user's finger and the touch sensor 110 by using a sensor value of the touch sensor 110 in operation 1050.

The blood pressure measuring apparatus 100 may determine whether the obtained additional information satisfies a predetermined criterion; and upon determination, in response to the additional information satisfying the predetermined criterion in operation 1060, the blood pressure measuring apparatus 100 may determine a blood pressure estimation value, which is estimated in operation 1040, to be a final blood pressure estimation value, and may terminate a blood pressure estimating process.

By contrast, in response to the additional information not satisfying the predetermined criterion in operation 1060, the blood pressure measuring apparatus 100 may adjust, in 1070, reliability of the blood pressure estimation value which is estimated in 1040, and may terminate a blood pressure estimating process.

Figure 11:
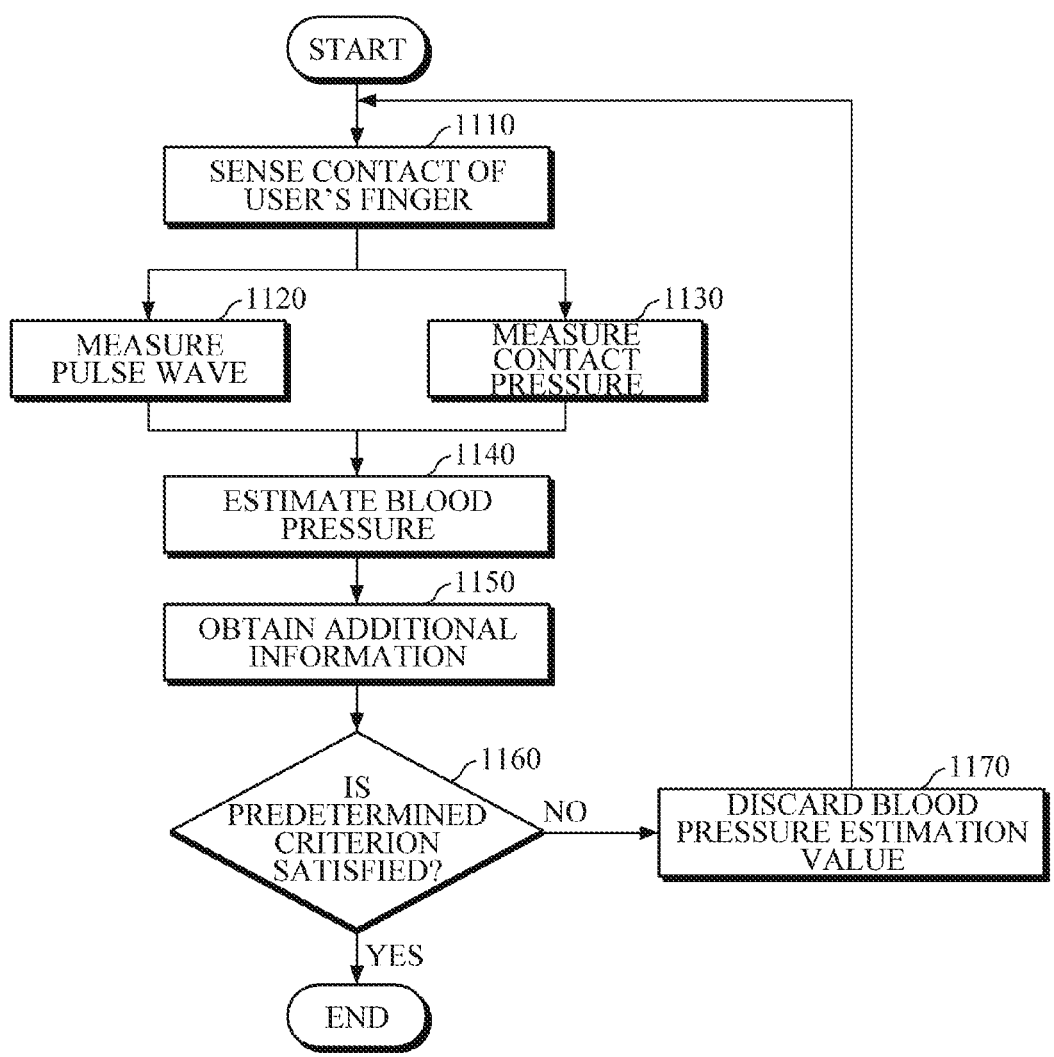
FIG. 11 is a flowchart illustrating a blood pressure estimating method according to another exemplary embodiment.

FIG. 11 is a flowchart illustrating still another example of a blood pressure estimating method. The blood pressure estimating method of FIG. 11 may be performed by the blood pressure measuring apparatus of FIG. 1.

Referring to FIGS. 1 and 11, the blood pressure measuring apparatus 100 may sense contact of a user's finger with the touch sensor 110 in operation 1110.

The blood pressure measuring apparatus 100 may measure pulse waves of the user by transmitting and receiving light to and from the user's finger touching the touch sensor 110 in operation 1120.

The blood pressure measuring apparatus 100 may measure contact pressure between the user's finger and the touch sensor 110 in operation 1130.

The blood pressure measuring apparatus 100 may estimate blood pressure of the user by analyzing a change in pulse waves according to the measured contact pressure in operation 1140.

The blood pressure measuring apparatus 100 may obtain additional information on a contact state between the user's finger and the touch sensor 110 by using a sensor value of the touch sensor 110 in operation 1150.

The blood pressure measuring apparatus 100 may determine whether the obtained additional information satisfies a predetermined criterion; and upon determination, in response to the additional information satisfying the predetermined criterion in operation 1160, the blood pressure measuring apparatus 100 may determine the blood pressure estimation value, which is estimated in operation 1140, to be a final blood pressure estimation value, and may terminate a blood pressure estimating process.

In operation 1170, in response to the additional information not satisfying the predetermined criterion in operation 1160, the blood pressure measuring apparatus 100 may discard the pulse waves measured in operation 1120 and the blood pressure estimation value which is estimated in operation 1140, and may return to operation 1110 to sense contact of the user's finger.

Figure 12:
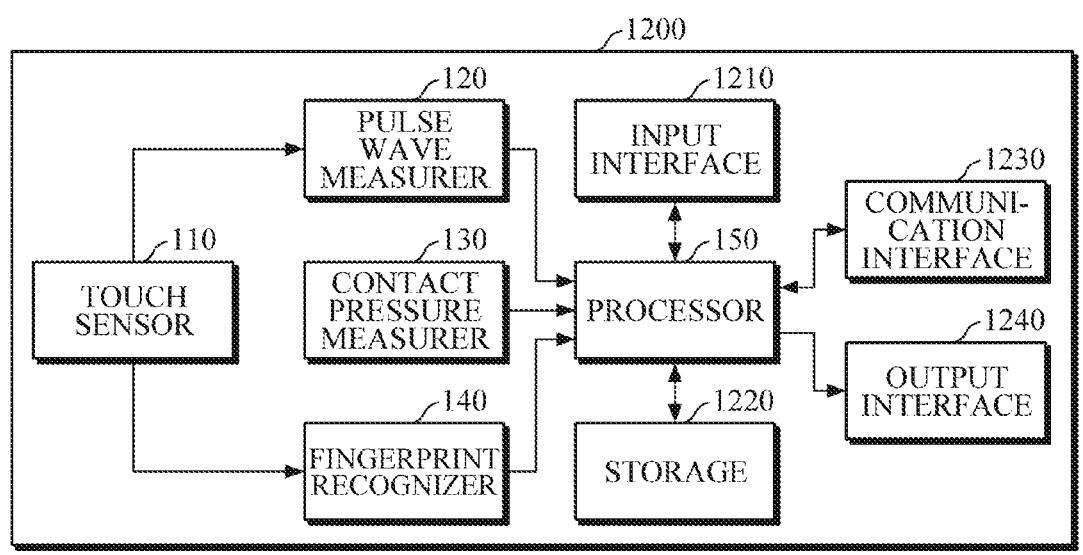
FIG. 12 is a block diagram illustrating a blood pressure measuring apparatus according to another exemplary embodiment.

FIG. 12 is a block diagram illustrating another example of a blood pressure measuring apparatus.

Referring to FIG. 12, the blood pressure measuring apparatus 1200 includes a touch sensor 110, a pulse wave measurer 120, a contact pressure measurer 130, a fingerprint recognizer 140, a processor 150, an input interface 1210, a storage 1220, a communication interface 1230, and an output interface 1240.

Here, the touch sensor 110, the pulse wave measurer 120, the contact pressure measurer 130, the fingerprint recognizer 140, and the processor 150 are described above with reference to FIGS. 1 to 8, such that detailed description thereof will be omitted.

The input interface 1210 may receive input of various operation signals from a user. In one embodiment, the input interface 1020 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 1220 may store programs or commands for operation of the blood pressure measuring apparatus 1200, and may store data input to and output from the blood pressure measuring apparatus 1200. Further, the storage 1220 may store data obtained or processed by each of the components 110 to 150, and information required for processing data of each of the components 110 to 150.

The storage 1220 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the blood pressure measuring apparatus 1200 may operate an external storage medium, such as web storage and the like, which performs a storage function of the storage 1220 on the Internet.

The communication interface 1230 may perform communication with an external device. For example, the communication interface 1230 may transmit, to the external device, data input by a user through the input interface 1210, the data obtained or processed by each of the components 110 to 150, and the information required for processing data of each of the components 110 to 150, and the like; or may receive, from the external device, various data useful for estimation of blood pressure.

In this case, the external device may be medical equipment using the data input by a user through the input interface 1210, the data obtained or processed by each of the components 110 to 150, and the information required for processing data of each of the components 110 to 150, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 1230 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The output interface 1240 may output the data input by a user through the input interface 1210, the data obtained or processed by each of the components 110 to 150, and the information required for processing data of each of the components 110 to 150, and the like. In one embodiment, the output interface 1240 may output the data input by a user through the input interface 1210, the data obtained or processed by each of the components 110 to 150, and the information required for processing data of each of the components 110 to 150, and the like, by using at least one of an acoustic method, a visual method, and a tactile method. To this end, the output interface 1240 may include a display, a speaker, a vibrator, and the like.

Figure 13:
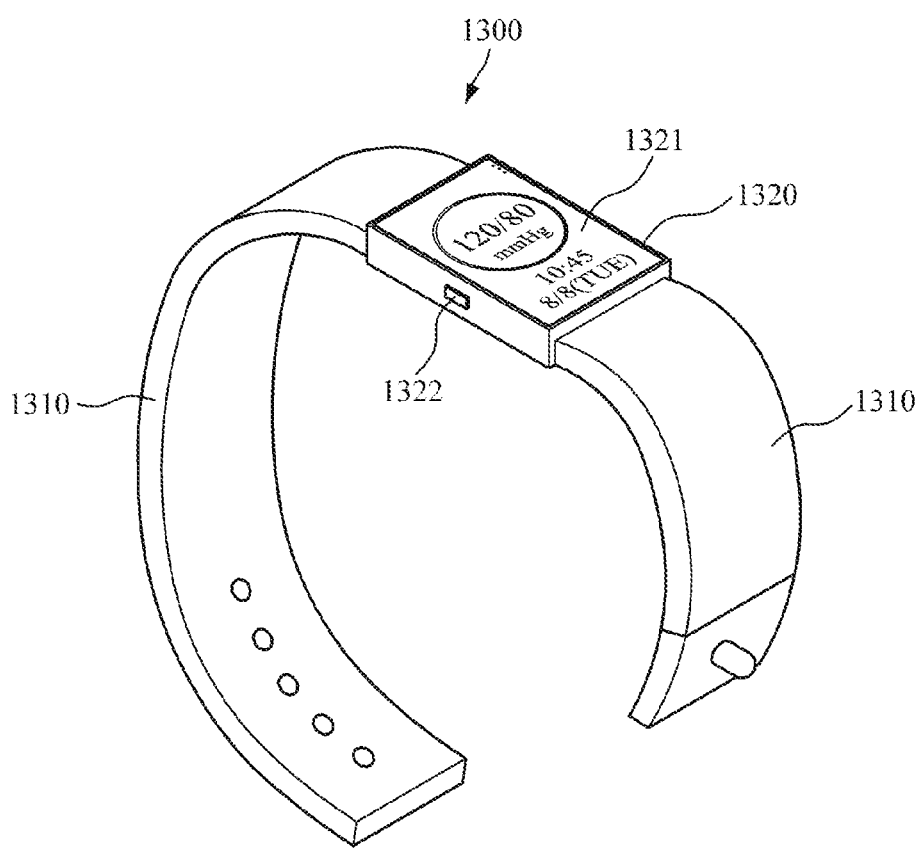
FIG. 13 is a diagram illustrating a wrist-type wearable device according to an exemplary embodiment.

FIG. 13 is a diagram illustrating a wrist-type wearable device.

Referring to FIG. 13, the wrist-type wearable device includes a strap 1310 and a main body 1320.

The strap 1310 may be connected at both sides of the main body 1320, and both ends of the strap 1310 may be detachably connected or may be integrally formed as a smart band strap. The strap 1310 may be made of a flexible material to wrap around a user's wrist so that the main body 1320 may be worn around a user's wrist.

The main body 1320 may include the above-described blood pressure measuring apparatuses 100 and 1200. Further, the main body 1320 may include a battery which supplies power to the wrist-type wearable device 1300 and the blood pressure measuring apparatuses 100 and 1200.

The touch sensor may be mounted at the top of the main body 1320 to be exposed so that a user's finger may easily touch the touch sensor. However, the touch sensor is not limited thereto, and may be mounted at the strap 1310.

The wrist-type wearable device 1300 may further include a display 1321 and an input interface 1322 which are mounted at the main body 1320. The display 1321 may display data processed by the wrist-type wearable device 1300 and the blood pressure measuring apparatuses 100 and 1200, processing result data thereof, and the like. The input interface 1322 may receive input of various operation signals from a user.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A blood pressure measuring apparatus comprising:
    a touch sensor configured to output a touch signal when a touch is detected;
    a pulse wave measurer configured to measure pulse waves from a finger of a user when the finger is in contact with a contact surface of the touch sensor;
    a force sensor configured to measure a contact pressure between the finger and the touch sensor; and
    a processor configured to:
        recognize a fingerprint of the finger based on the touch signal;
        determine a degree of position coincidence between the finger and the pulse wave measurer based on the recognized fingerprint;
        identify a center of gravity of the contact surface of the touch sensor when the touch sensor is in contact with the finger; and
        in response to the degree of position coincidence between the finger and the pulse wave measurer being greater than a predetermined threshold value, and the center of gravity of the contact surface satisfying a predetermined criterion, estimate a blood pressure of the user based on the pulse waves and the contact pressure.

2. The blood pressure measuring apparatus of claim 1, wherein the touch sensor comprises a first area for recognizing the fingerprint and a second area that surrounds the first area,
    a plurality of sensing lines and a plurality of driving lines are provided in the first area and the second area, and
    a space interval between the plurality of sensing lines and a space interval between the plurality of driving lines in the first area are narrower in the first area than in the second area.

3. The blood pressure measuring apparatus of claim 2, wherein the first area has a higher resolution than a resolution of the second area.

4. The blood pressure measuring apparatus of claim 2, wherein the processor is further configured to recognize the fingerprint by using a sensor value of the first area.

5. The blood pressure measuring apparatus of claim 1, wherein the pulse waves comprise photoplethysmogram.

6. The blood pressure measuring apparatus of claim 1, wherein the processor is further configured to determine a position of the finger by comparing the recognized fingerprint with pre-stored reference fingerprint information.

7. The blood pressure measuring apparatus of claim 6, wherein the processor is further configured to determine the degree of position coincidence between the finger and the pulse wave measurer by determining whether a central portion of the finger is positioned on the pulse wave measurer based on the determined position of the finger.

8. The blood pressure measuring apparatus of claim 1, wherein the processor is further configured to:
    in response to the determined degree of position coincidence not exceeding the predetermined threshold value, discard the measured pulse waves.

9. The blood pressure measuring apparatus of claim 1, wherein the processor is further configured to, in response to the determined degree of position coincidence being less than or equal to the predetermined threshold value, adjust reliability of a pre-estimated blood pressure estimation value by using a model that defines a relationship between the degree of position coincidence and blood pressure estimation reliability.

10. The blood pressure measuring apparatus of claim 1, wherein the processor is further configured to, in response to the identified center of gravity of the contact surface not satisfying the predetermined criterion, adjust reliability of a pre-estimated blood pressure estimation value by using a model that defines a relationship between the degree of position coincidence and blood pressure estimation reliability.

11. A blood pressure measuring method comprising:
    sensing contact between a finger of a user and a touch sensor;
    measuring, using a pulse wave measurer, pulse waves from the finger when the finger is in contact with a contact surface of the touch sensor;
    measuring a contact pressure between the finger and the touch sensor;
    recognizing a fingerprint of the finger;
    determining a degree of position coincidence between the finger and the pulse wave measurer based on the recognized fingerprint;
    identifying a center of gravity of the contact surface of the touch sensor when the touch sensor is in contact with the finger; and
    in response to the degree of position coincidence between the finger and the pulse wave measurer being greater than a predetermined threshold value, and the center of gravity of the contact surface satisfying a predetermined criterion, estimating a blood pressure of the user based on the pulse waves and the contact pressure.

12. The blood pressure measuring method of claim 11, wherein the touch sensor comprises a first area for recognizing the fingerprint and a second area that surrounds the first area;
    a plurality of sensing lines and a plurality of driving lines are provided in the first area and the second area, and a space interval between the plurality of sensing lines and a space interval between the plurality of driving lines in the first area are narrower in the first area than in the second area, so that the first area has a higher resolution than a resolution of the second area.

13. The blood pressure measuring method of claim 12, wherein the recognizing the fingerprint comprises recognizing the fingerprint by using a sensor value of the first area.

14. The blood pressure measuring method of claim 11, wherein the determining the degree of position coincidence comprises:
   determining a position of the finger by comparing the recognized fingerprint with pre-stored reference fingerprint information; and
   determining the degree of position coincidence between the finger and the pulse wave measurer by determining whether a central portion of the finger is positioned on the pulse wave measurer based on the determined position of the finger.

15. The blood pressure measuring method of claim 11, wherein the estimating the blood pressure of the user comprises:
   in response to the determined degree of position coincidence being less than or equal to the predetermined threshold value, adjusting reliability of a pre-estimated blood pressure estimation value by using a model that defines a relationship between the degree of position coincidence and blood pressure estimation reliability.

* * * * *